US006333033B1

(12) United States Patent
Genain et al.

(10) Patent No.: US 6,333,033 B1
(45) Date of Patent: Dec. 25, 2001

(54) AUTOANTIBODY INHIBITORS

(75) Inventors: Claude P. Genain, Mill Valley; Stephen L. Hauser, Ross, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/384,036

(22) Filed: Aug. 26, 1999

Related U.S. Application Data

(60) Provisional application No. 60/097,953, filed on Aug. 26, 1998.

(51) Int. Cl.[7] ................................................. A61K 39/395
(52) U.S. Cl. ................................... 424/137.1; 424/130.1; 424/141.1; 424/809; 424/810; 424/133.1; 424/152.1; 424/172.1; 514/903
(58) Field of Search ............................ 424/141.1, 137.1, 424/130.1, 809, 810, 133.1; 514/903; 530/387.1, 388.1, 387.3, 389.1, 382.5

(56) References Cited

U.S. PATENT DOCUMENTS 5,783,216 * 7/1998 Faustman .

FOREIGN PATENT DOCUMENTS

WO 95/07096    3/1995 (WO) .

OTHER PUBLICATIONS

Nicholson et al. A T Cell Receptor Antagonist peptide Induces T Cells that Mediate Bystander Suppression and Prevent Autoimmune Encephalomeylitis Induced with Multiple Myelin Antigens. Proc. Natl. Acad. Sci. USA. Aug. 1997, vol. 94, pp. 9279–9284.

Linington et al. The Role of Complement in the Pathogenesis of Experimental Allergic Encephalomyelitits. Brain. 1989, vol. 112, pp. 895–911.

Genain et al. Antibody Facilitation of Multiple Sclerosis –like Lesions in a Nonhuman Primate. J. Clin. Invest. Dec. 1995, vol. 96, pp. 2966–2974.

Litzenburger et al. B Lymphocytes Producing Demyelinating Autoantibodies: Development and Function in Gene–Targeted Transgenic Mice. Journal of Experimental Medicine. Jul. 6, 1998, vol. 188, No. 1, pp. 169–180.

Smilek et al. Proc. Natl. Acad. Sci. USA (1991) 88:9633–9637.*

Tisch et al. Proc. Natl. Acad.l Sci. USA 1994 91:437–438, Jan. 1994.*

Vincent et al. J. Neuroimmunolog. 1999 100:169–180, 1999.*

* cited by examiner

Primary Examiner—Phillip Gambel
Assistant Examiner—Jessica H. Roark
(74) Attorney, Agent, or Firm—Richard Aron Osman

(57) ABSTRACT

The invention provides methods and compositions for inhibiting pathogenic binding of an pathogenic autoantibody to a myelin oligodendrocyte glycoprotein (MOG) autoantigen and screening for inhibitors of pathogenic binding of an autoantibody to a MOG autoantigen.

2 Claims, No Drawings

AUTOANTIBODY INHIBITORS

RELATED APPLICATIONS

This application claims priority to U.S. Provisional Application 60/097,953 filed Aug. 26, 1998.

FIELD OF THE INVENTION

The field of this invention is polypeptide autoantibody inhibitors and methods of use thereof.

BACKGROUND

Multiple sclerosis (MS) is a chronic relapsing remitting disorder disease of the central nervous system that affects 350,000 Americans and, second to trauma, is the leading cause of disability among young adults. MS is an immune-mediated disorder characterized pathologically by perivenular white matter infiltrates comprised of macrophages and mononuclear cells (inflammation), and destruction of the myelin sheaths that insulate nerve fibers (demyelination).

Experimental allergic encephalomyelitis (EAE) in rodents has been the most widely employed model for testing of therapies for human MS. These traditional disease models for MS generally have promoted the concept that MS is a T-cell-mediated disorder. However, the autoantigens that serve as targets for the immune attack have not been identified and the molecular mechanisms implicated in myelin damage remain uncertain. While it is clear that CNS inflammation in EAE is initiated by autoagressive T-cells that recognize myelin antigens in the context of class II-MHC molecules, many of the models lack the early demyelinating component of the MS lesion. B-cell activation and antibody responses appear necessary for the full development of EAE and earlier studies on immune mediated demyelination using myelinated cultures of CNS tissue have implicated humoral factors as effector mechanisms. Thus, it is not surprising that rodent EAE has not been a robust predictor of efficacy in humans as fundamental differences in the clinical course, pathology, and immunologic response to myelin proteins distinguish rodent EAE from human MS.

Recently a novel MS-like illness in an outbred nonhuman primate, the common marmoset *Callithrix jacchus*, has been defined. The marmoset EAE has a prominent, MS-like early demyelinating component which requires the presence of myelin-specific autoantibodies, and has afforded an opportunity to understand the interactions between these antibodies and their target antigens on myelin. Characteristics of the model include: a. Mild clinical signs and a relapsing remitting course similar to MS; b. A primary demyelinating pathology with early gliosis indistinguishable from MS lesions (demyelinating plaques); c. Natural bone marrow chimerism permitting successful adoptive transfer of encephalitogenic (e.g disease-inducing) T-cell clones and lines; d. Diversity of the encephalitogenic repertoire of T-cells reactive against fit the major myelin protein myelin basic protein (MBP); e. Different disease phenotypes resulting from immunization with different myelin constituents: in contrast to whole myelin, immunization with MBP produces a non-demyelinating form of EAE; f. Demonstration that demyelination is antibody-mediated but also requires an encephalitogenic T-cell response to facilitate autoantibody access to the nervous system; and, g. A key role of myelin oligodendrocyte glycoprotein (MOG) in plaque formation: adoptive transfer of anti-MOG antibody in non-demyelinating MBP-EAE reproduces fully developed MS-like pathology.

The highly immunogenic properties of MOG (<0.05% of total myelin protein) may be related to its extracellular location on the outermost lamellae of the myelin sheath, where it is accessible to pathogenic antibody in the context of blood brain barrier disruption by encephalitogenic T-cells. The *C. jacchus* model permits precise identification of cellular and humoral immune responses that result in an MS-like lesion in a species with immune and nervous system genes that are 90–95% homologous to humans. The relevance of this model to human MS is emphasized by the recent finding of strong T-cell and antibody responses to MOG in MS patients.

SUMMARY OF THE INVENTION

The present invention is directed to autoantibody inhibitors and methods of use thereof Accordingly, the invention provides methods and compositions for inhibiting pathogenic binding of an autoantibody to an autoantigen and screening for inhibitors of pathogenic binding of an autoantibody to an autoantigen.

In one aspect, the present invention provides a composition comprising a peptide consisting of residues 28–36, 13–21, 62–74, 27–34 or 40–45 of rat, human or marmoset MOG. In a preferred embodiment the MOG polypeptide is directly joined at its N- and C- termini with other than natural human or marmoset MOG flanking residues.

In another aspect, the present invention provides a method of inhibiting pathogenic binding of a MOG specific autoantibody to MOG or an immunodominant epitope thereof.

In yet another aspect, the present invention provides a method of detecting autoantibodies in a tissue sample. In a preferred embodiment a method of identifying autoantibodies against myelin/oligodendrocyte glycoprotein (MOG) within lesions of human MS and *C. jacchus* EAE, where they appear to be directly responsible for the disintegration of the myelin sheaths, is provided.

In a further aspect, the present invention provides a method of screening small molecules or candidate agents capable of binding to an autoantigen and thereby inhibit binding of an autoantibody. The method comprises contacting a solution comprising an autoantigen and an autoantibody, incubating under conditions sufficient to allow the reaction to reach equilibrium, and comparing the binding of the autoantibody in the absence of the small molecule inhibitor or candidate agent to the binding of the autoantibody in the presence of the small molecule inhibitor or candidate agent. In a preferred embodiment the small molecules specifically bind at least one immunodominant epitope of the autoantigen.

In yet another aspect of the invention there is provided a method of inhibiting pathogenic binding of an autoantibody to an autoantigen comprising administering to a host subject to pathogenic autoantigen-autoantibody binding-mediated pathology an effective amount of a composition comprising a fragment of an antibody specific for the autoantigen sufficient to specifically bind the autoantigen and competitively inhibit the binding of an autoantigen-specific autoantibody to the autoantigen, wherein the fragment does not comprise a functional Fc portion of the autoantigen-specific antibody. In a preferred embodiment, the autoantigen-autoantibody binding is associated with a demyelinating disease of the central or peripheral nervous system. In a particular embodiment, the disease is associated with pathogenic autoantibody binding, such as MS, lupus, arthritis or diabetes. In more particular embodiments, the autoantigen is a MOG autoantigen and the fragment is a F(ab')$_2$ fragment.

In yet another aspect, the invention also provides methods of screening for an agent which modulates the binding of an autoantibody to an autoantigen. Such methods generally involve incubating a mixture comprising the autoantibody or an auto antibody-specific binding fragment thereof, the autoantigen, and a candidate agent under conditions whereby, but for the presence of said agent, the autoantibody or fragment thereof specifically binds the autoantigen at a reference affinity; detecting the binding affinity of autoantibody or fragment thereof to the autoantigen to determine an agent-biased affinity, wherein a difference between the agent-biased affinity and the reference affinity indicates that said agent modulates the binding of the autoantibody or fragment thereof to the autoantigen. In particular embodiments, the autoantibody or fragment thereof is a $F(ab')_2$ fragment; the autoantigen comprises a MOG epitope; and/or the autoantigen comprises a MOG epitope consisting of residues 28–36, 13–21, 62–74, 27–34 or 40–45 of rat, human or marmoset MOG.

DETAILED DESCRIPTION OF THE INVENTION

The following description and examples are offered by way of illustration and not by way of limitation.

The invention provides methods and compositions for inhibiting pathology associated with the binding of an autoantibody to a MOG polypeptide, such as occurs in MS. The general methods comprise the step of administering to a host, subject to a pathogenic MOG polypeptide—autoantibody binding, an effective amount of a composition comprising a MOG polypeptide-specific antibody fragment not having a functional Fc portion and sufficient to specifically bind the MOG polypeptide and competitively inhibit the binding of the autoantibody to the MOG polypeptide, whereby the pathology is inhibited. In a particular embodiment, the fragment is selected from the group consisting of Fv, $F(ab')_2$, F(ab), $F(ab)_2$ or fragments thereof The compositions include pharmaceutical compositions comprising a MOG polypeptide-specific antibody fragment sufficient to specifically bind a natural MOG polypeptide and competitively inhibit the binding of an autoantibody to the MOG polypeptide, wherein the fragment does not comprise a functional Fc portion, and a pharmaceutically acceptable carrier. The compositions may also comprise a MOG tolerogenic T-cell epitope which induces tolerance and acts synergistically with the antibody fragment to inhibit pathology.

In another embodiment, the invention provides methods and compositions for detecting the presence of an autoantibody bound to a first autoantigen in a tissue. These methods generally comprise the steps of contacting the tissue with a second, labeled autoantigen under conditions wherein the autoantibody binds the second autoantigen to form first autoantigen-autoantibody-second autoantigen labeled complexes, and specifically detecting the labeled complexes. The first and second autoantigens are generally the same or at least include epitopes of the same autoantigen. Preferred autoantigens include, but are not limited to myelin oligodendrocyte glycoprotein (MOG), myelin associated glycoprotein (MAG), myelin/oligodendrocyte basic protein (MOBP), Oligodendrocyte specific protein (Osp), myelin basic protein (MBP), proteolipid apoprotein (PLP), galactose cerebroside (GalC), glycolipids, sphingolipids, phospholipids, gangliosides and other neuronal antigens.

In yet another embodiment, the invention provides methods and compositions for detecting MOG polypeptide-specific B-cells. Such methods generally comprise the steps of fractionating blood to obtain an unselected population of B-cells comprising rare MOG polypeptide-specific B-cells, contacting the population with labeled MOG polypeptides under conditions whereby the labeled MOG polypeptides binds the rare MOG polypeptide-specific B-cells to form labeled complexes of the labeled MOG polypeptides and the rare MOG polypeptide-specific B-cells, and specifically detecting the complexes.

In yet another embodiment, the invention provides methods and compositions for screening for a candidate agent to inhibit pathology associated with MOG polypeptide-specific antibody binding to a MOG polypeptide. These methods generally comprise the steps of:

incubating a mixture comprising: the antibody or a MOG-specific fragment thereof, the MOG polypeptide, and a candidate agent, under conditions whereby, but for the presence of said agent, the antibody or fragment thereof specifically binds the MOG polypeptide at a reference affinity;

detecting the binding affinity of antibody or fragment thereof to the MOG polypeptide to determine an agent-biased affinity, wherein a diminution of the agent-biased affinity with respect to the reference affinity indicates that said agent inhibits the binding of the antibody or fragment thereof to the MOG polypeptide and provides a candidate agent for inhibiting pathology associated with MOG polypeptide-specific antibody binding to a MOG polypeptide.

In yet another embodiment, the invention provides polypeptides comprising MOG-specific B- and T-cell epitopes, including polypeptides comprising a fragment having N and C ends and consisting of residues 28–36, 13–21, 67–73, 27–34 or 40–45 of human, rat or marmoset MOG, wherein the fragment is directly joined at at least one of the N and C-ends with other than natural human or marmoset MOG flanking residues. Such polypeptides are useful, for example in methods of inhibiting MOG polypeptide-autoantibody binding, such as the general method sol comprising the step of contacting a mixture of a MOG and an antibody with a polypeptide, whereby the MOG-antibody binding is inhibited.

As used herein, the term "antibody" refers to recombined immune proteins such as T-cell antigen receptors and immunoglobulins, as well as chimeric, humanized or other recombinant antibodies. As used herein, the term "antibody fragment" refers to fragments of antibodies such as Fab, Fab', $F(ab)_2$, $F(ab')_2$ and Fv or any combination thereof. Fv and fragments thereof may be monovalent or divalent. Fv is also known in the art as a minimal antibody fragment. Methods of making antibody fragments, particularly F(ab') are known in the art. (See for example, Harlow and Lane, Antibodies: A Laboratory Manual, Cold Spring Harbor Laboratory, New York (1988), incorporated herein by reference). For example, F(ab), Fv, etc. can also be produced by recombinant technology.

As used herein, "other than natural human or marmoset MOG flanking residues" refers to anything other than residues naturally flanking the recited peptides in the native proteins. For example, other than natural flanking residues includes no flanking residues or flanking residues different from what naturally flanks the recited peptide.

MOG was originally identified by the mouse monoclonal antibody 8.18.C5, raised against rat cerebellar glycoproteins. It is a quantitatively minor protein representing only 0.01 to 0.05% of the total myelin proteins and has no known function within the CNS. MOG is a member of the immunoglobulin (Ig) superfamily, with an immunoglobulin-like, extracellular domain comprised of 121 amino acids containing one glycosylation site (Asn in position 31) and two highly hydrophobic regions that could represent transmembrane domains, for a total length of 224 amino acids. MOG is widely expressed on oligodendrocyte cell bodies and processes, especially on the outermost layers of the myelin sheaths, and may be more readily accessible to antibody attack than intra-cytoplasmic MBP, or intra and intermembranous proteolipid apoprotein (PLP). In all species studied including C. jacchus, the non-glycosylated, recombinant extracellular domain of MOG (rMOG) which is highly conserved, suffices for sensitizing animals for EAE. In one aspect of the invention, we have identified minimal T-cell and B-cell epitopes, including residues 28–36, 13–21, 62–74, 27–34 or 40–45; natural human and rat MOG sequences are known in the art; natural marmoset MOG is identical to the human except for the following substitutions: 9S, 13Q, 19A, 20A, 42S, 60E, 75D, 84K, 91P, 112Q, 137F, 148Y and 151H.

The immune response in autoimmune diseases may possess both cellular and humoral components. Our data indicate that the following sequence of events leads to myelin destruction in CNS autoimmune demyelination:

1) Myelin vacuolation caused by soluble mediators (cytokines, antibodies, free radicals), and/or cellular cytotoxicity. A pattern of intramyelinic edema similar to this has also been observed previously in the CNS of rats intoxicated with tri-ethyl tin sulfate and, interestingly, these changes were reversible.

2) Transformation of vacuolated myelin into networks of small vesicles separated by 2–3 layers of altered myelin with a reduced periodicity (5–6 nm). This dramatic transformation appears to be associated with the deposition of MOG-specific IgG and to reflect antibody-mediated damage, possibly due to complement activation, or antibody-dependent cytotoxicity mediated by macrophages that are invariably associated with vesicular myelin disruption. Conceivably, the initial vacuolar lesion renders the myelin membranes accessible to an attack by autoantibodies.

3) Macrophage activation leading to receptor-mediated phagocytosis of the vesiculated myelin debris. This mechanism has been demonstrated previously in MS and in EAE with IgG serving as a ligand between the myelin debris and Fc receptors in clathrin-coated pits on the macrophage surface. This stage of lesion pathogenesis, although antibody-mediated, may be independent of antibody specificity.

As just outlined above, for example, in MS the inflammatory component is T-cell mediated while the demyelinating component appears to be B-cell mediated. Thus, effective treatments should address both components.

The present invention provides compositions comprising the immunodominant epitopes of MOG. The abolition of the peripheral T-cell response by a tolerization protocol to the extracellular portion of recombinant MOG (aa 1–125) (rMOG; rMOG is comprised of residues 1–125 of the extracellular amino terminus of MOG extended by MRGS at the $NH_2$ and $ASES(H)_6$ at the COOH termini) provided the basis for the present inventive epitope-derived peptide compositions. Mapping of the critical MOG epitopes (including 26–38 and 64–72) was accomplished by cloning T-cells from rMOG-immunized animals and by analyzing T-cell and antibody responses to short peptides of MOG in rMOG immunized marmosets.

Mapping of the antibody response to MOG in C. jacchus indicates limited heterogeneity of epitope recognition by autoantibodies. We have identified regions of MOG that are targeted by demyelinating antibodies using linear peptides. The native, serum polyclonal antibodies in rMOG-immunized marmosets are directed against 4 discrete epitopes along the amino acid sequence, aa 13–21, 28–34, 40–45, 65–74 or shorter sequences, most of which are conserved sequences across species. These peptides differ from those identified to date as antibody epitopes in rodents (aa 35–55), however they bind to antibodies present within the network of vesiculated myelin in acute lesions of human MS as shown in the Examples below. Because most antibodies generally recognize discontinuous epitopes on proteins, our analysis methodology provides detailed knowledge of the structure of MOG is needed to fully define the antigenic repertoire of demyelinating antibodies in C. jacchus and humans. Combinatorial libraries were then made in order to generate $F(ab')_2$ fragments with high affinity for MOG capable of competing with pathogenic IgG and of inhibiting complement-mediated and antibody dependent cellular cytotoxicity. These $F(ab')_2$ fragments were tested alone and in combination with T-cell tolerogenic peptides for their ability to prevent and treat disease in C. jacchus.

A recently identified patient with a progressive spinal cord disorder associated with an IgG monoclonal gammopathy reactive to MOG offered a unique example of the pathophysiologic consequences of an anti-MOG antibody response in a natural experiment. The human monoclonal antibody was adoptively transferred into a C. jacchus with non-demyelinating EAE. Following adoptive transfer the marmoset developed demyelination. Transfer of human IgG in this species is well-tolerated and the blocking ability of $F(ab')_2$ fragments is demonstrated in the adoptive transfer system. The antibody fragments retain their ability to recognize antigenic epitopes yet lack the ability to activate complement or bind macrophages, they coat the autoantigen such that the endogenous autoantibodies are unable to bind a pathological level.

In the preparation of the pharmaceutical compositions of this invention, a variety of vehicles and excipients and routes of administration may be used, as will be apparent to the skilled artisan. Representative formulation technology is taught in, inter alia, Remington: The Science and Practice of Pharmacy, 19th ed., Mack Publishing Co., Easton, Pa., 1995; e.g. Goodman & Gilman's The Pharmacological Basis of Therapeutics, $9^{th}$ Ed., 1996, McGraw-Hill.

EXAMPLES

The following examples are offered to illustrate this invention and are not meant to be construed in any way as limiting in scope of this invention.

We show that antibodies against MOG that cause demyelination in marmosets may be modified chemically and used as therapeutic tools to competitively block the binding of real-life, pathogenic antibody. This is achieved by enzymatic digestion, e.g., with pepsin, which cleaves the intact antibody into a large fragment ($F[ab']_2$) that contains the sites that bind to the target antigen (MOG), and smaller fragments including the Fc portion, a portion of antibodies known to contain receptors for systems such as complement and macrophages (also known to mediate many pathogenic or cytotoxic properties of antibodies). Thus, the $F(ab')_2$ retains the capacity to bind to MOG in the brain, but is devoid of capacity to Fc complement or activate macrophages and protects/masks MOG otherwise recognized by the pathogenic antibodies. In a particular example, a pair of marmosets were first sensitized to EAE with MBP (non-demyelinating), then both given intravenous demyelinating antibody (mouse monoclonal 8.18.C5) against MOG. Simultaneously, one animal (control) received a placebo F(ab')$_2$ injection, and the other received F(ab')$_2$ fragments prepared from the same demyelinating antibody. The control animal showed aggravation of the clinical signs of EAE and the experimental animal did not. The animals were sacrificed 3–5 days later and histology of the brain and spinal cord obtained. The control animal had evidence of demyelinating lesions, and the experimental animal had lesions with inflammation (cellular infiltration) but no demyelination (no myelin destruction). This experiment shows that marmosets can be protected from antibody mediated demyelination by MOG-specific F(ab')$_2$ fragments.

Complementary experiments of the above indicate that such therapeutic principle of F(ab')$_2$ or F(ab') fragments could be useful for human MS or related disorders: antibodies against MOG are intimately associated with active lesions of MS where there is morphologic evidence for the ongoing disintegration of myelin (see "Identification of autoantibodies associated with demyelination in multiple sclerosis", below). In this work, the epitopes of MOG that are recognized by marmosets are also disclosed for the first time and this information is used to construct gold-conjugates as immunoprobes to identify the presence of MOG-specific autoantibodies in both primate and human tissues.

Induction of Marmoset EAE. EAE was induced in marmosets as described by Genain et al. (1999) Nature Medicine 5, 170–175. Six marmosets were actively sensitized with 50 to 100 μg of recombinant rat MOG dissolved in 100 μl of phosphate-buffered saline and emulsified with an equal volume of complete Freund's adjuvant (CFA) containing 3 mg/ml killed *Mycobacterium tuberculosis* (h37Ra; DIFCO, Detroit, Mich.). The MOG/CFA emulsion was given intradermally at four injection sites in the scapular and hip regions in a total volume of 0.2 ml. On the day of immunization with MOG/CFA, $1 \times 10^{10}$ inactivated *Bordetella pertussis* organisms in 2.5 ml of isotonic saline were given intravenously and the dose repeated 2 days later. For comparison, 4 marmosets sensitized with 200 mg of whole white matter (WM)/CFA and *B. pertussis* were examined between 18 and 39 days after immunization. MOG-sensitized marmosets were maintained for up to 93 days after immunization. Animals sensitized with either WM or MOG displayed signs of EAE within 21 days of immunization. The animals were sacrificed by intracardiac perfusion under deep anesthesia 18 to 93 days after immunization.

MS tissues from humans. Human CNS tissues were obtained from 3 subjects with MS by biopsy or autopsy (8 weeks, 11 years and 17 years after diagnosis). Patient 1 was an 18-year old Caucasian woman with a 3-month history of acutely developing right hemiplegia, sensory loss, and spasticity. Computed tomographic scanning revealed WM hypodensity in the left parieto-occipital region. A brain biopsy was performed for neuropathological evaluation. The resultant diagnosis was actively demyelinating, inflammatory, edematous lesions of recent origin, typical of a fulminant inflammatory demyelinating condition, consistent with acute MS.

Patient 2 was a 31 year old Caucasian female with an 8-year history of chronic progressive MS characterized by numbness and weakness of the limbs, gait disturbance, urinary incontinence, tremor, nystagmus, and blurred vision. Terminally, the patient was wheelchair-bound, developed seizures and aspiration pneumonia, and died. An autopsy was performed within 1.5 hours of death. Neuropathological examination revealed a predominance of small (3–5 mm), disseminated, recent, intensely inflamed, edematous, demyelinating lesions as well as larger, more established plaques with fibrous astrogliosis and well-demarcated edges.

Patient 3 was a 34-year old Caucasian female with a history of relapsing-remitting MS for 10 years after initial diagnosis at age 20. The disease entered a chronic progressive course for the last 7 years of her life. At the time of death, the patient presented with bilateral optic atrophy, internuclear ophthalmoplegia, spastic paraparesis, and moderate limb ataxia. The cause of death was respiratory failure. An autopsy was performed 4 hours after death. Neuropathology of this case revealed intensely inflammatory, edematous, actively demyelinating lesions of recent origin, as well as active chronically demyelinated lesions.

Tissue Preparation for Analysis. At the time of sampling, animals were sacrificed under pentobarbital anesthesia by intracardiac perfusion with 200 ml of phosphate-buffered saline followed by 150 to 200 ml of cold $PO_4$-buffered 2.5% glutaraldehyde. Two MOG-sensitized marmosets were sampled during the acute phase of the disease (14–16 days after immunization), 3 were taken after the acute phase, either during relapses or remission (23, 25 and 27 days after immunization), and 1 was examined after two relapses at 93 days after immunization. The 4 whole WM-sensitized animals were examined at 18, 30, 30 and 39 days after immunization after acute onset but before relapse. From the glutaraldehyde-perfused animals, the CNS was removed and routine neuropathology performed on formalin postfixed, paraffin-embedded material stained with hematoxylin and eosin, Lusol Fast Blue (for myelin), and the Bodian silver technique (for axons).

For fine structural analysis of marmoset tissues, 1-mm slices were taken form optic nerve, cerebral hemispheres, cerebellum, brainstem, medulla, and spinal cord at C7, T3, L2, L5, L6, and L7. In addition, samples were taken from spinal nerve roots and sciatic nerves. The slices of glutaraldehyde-fixed brain tissue were trimmed as flat rectangles (~4×6 mm) and spinal cord was left as whole slices. From the 3 cases of MS describe in Example 2, small pieces of biopsy tissue or slices of autopsied CNS material, 3 to 5 mm thick, were immersion-fixed for 4 to 24 hours at 4° C., then cut into thin, 1-mm slices to 3 to 5 mm in diameter. Glutaraldehyde-fixed tissues were then postfixed in $PO_4$-buffered 1% $OsO_4$ for 1 hour on ice. Samples were dehydrated, cleared in propylene oxide, and embedded flat in epoxy resin. Thin (1 μm) sections of epoxy-embedded tissue were prepared for light microscopy (LM) and stained with toluidine blue or reacted for immunocytochemistry. For electron microscopy (EM), sections were placed on copper grids, contrasted with lead and uranium salts (lead citrate and uranyl acetate), carbon-coated, and scanned in a Siemens 101 or Hitachi H 600-S.

Ultrastructural patterns of demyelination are identical in *C. jacchus* EAE and in acute MS plagues. CNS tissues from 6 *C. jacchus* marmosets with MOG-induced EAE and from 3 human subjects with MS, all showing acute lesions, were examined by electron microscopy (EM). In marmoset EAE, large demyelinated plaques up to several mm in diameter were disseminated throughout the CNS, invariably centered on venules and characterized by perivascular inflammation and a prominent margin along which many myelinated nerve fibers displayed vacuolated myelin sheaths. This typical pattern of myelin vacuolation resulted from the enlargement of individual myelin sheaths due to interlamellar splitting and swelling, with the axon displaced to one side surrounded by several layers of intact myelin. Micrographs showing the optic nerve from an animal with acute EAE induced by immunization with 50 µg of recombinant rat MOG in adjuvant, sacrificed 3 days after onset of clinical signs demonstrated the presence of large intramyelinic vacuoles at the perimeter of a demyelinated lesion, with axons surrounded by normal-appearing myelin sheaths elsewhere.

Between the lesion center and the margin was a broad zone of demyelination containing macrophages laden with myelin debris. The most striking finding was the presence within the demyelinated zone of large numbers of axons surrounded by aggregates of disrupted myelin rearranged as an expanded network. These axons were displaced laterally as the membranous network gradually became dissociated from the axon and taken up by adjacent macrophages.

Demyelination of fibers in acute MS was structurally identical to that seen in marmoset EAE, with the demyelinated axon lying within a membranous network of myelin. Elsewhere in the edematous parenchyma, free floating aggregates of myelin debris were common. Electron photomicrographs of tissue taken from a subcortical white matter biopsy from an 18-year old female patient with an 8-week history of neurologic signs, white matter hypodensity on MRI scan and a diagnosis of acute MS showed myelin around axons transformed into a vesicular network similar to that described above. Fibrous astroglial processes, naked axons and a reactive, ameboid microglial cell (below), were also identified. High resolution analysis of the myelin networks in both marmoset EAE and human MS revealed vesicles surrounded by 2 to 3 layers of loosely compacted membranes with a reduced periodicity (5–6 nm) when compared to intact myelin in normal tissue.

MOG-specific autoantibodies are associated with myelin vesiculation in the *C. jacchus* EAE lesion. MOG is a quantitatively minor myelin protein (less than 0.05% of total myelin proteins) with an immunoglobulin (Ig)-like extracellular domain that is expressed in abundance on the outermost layer of myelin sheaths, which may render it accessible to antibody attack. Although autoantibodies against MOG have been shown to enhance demyelination in several EAE models, the detailed interactions between these antibodies and myelin membranes has not been investigated. To identify the sites of autoantibody binding within demyelinating lesions, we performed immunocytochemistry on frozen and epoxy-embedded marmoset CNS tissue with gold-labeled anti-human IgG antibody (cross-reactive with marmoset IgG) followed by silver enhancement.

For the demonstration of antigen-specific autoantibodies in marmoset and human MS tissue in situ, a selection of myelin-related and control peptides were directly coupled to immunogold and applied to tissue sections. Immunogold labeling was performed on ultra-thin sections of frozen or fixed tissues. Gold conjugates were prepared of (1) three MOG peptides (amino acids [aa] 1–20, aa 21–40, and aa 41–60 of human MOG) with known encephalitogenic activity in marmosets; (2) one MOG peptide that has been shown not to be encephalitogenic in marmosets (aa 101–120); (3) one human myelin basic protein (MBP) peptide (aa 82–101) that is encephalitogenic in marmosets and immunodominant in humans with the DR2 haplotype; and, as a control, (4) a peptide of mouse serum albumin (MSA; aa 560–574). Peptides having human MOG subsequences were synthesized using standard Fmoc chemistry and purified (>95%) by HPLC (Research Genetics Inc., Huntsville, AL): MOG 1–20, MOG 21–40, MOG 61–80, MBP 82–101, and MSA 560–574. The gold conjugates were synthesized by using monosulfo-N-hydroxy succinimide-Nanogold labeling reagent (particle diameter, 1.4 nm), according to the manufacturer's instructions (Nanoprobes, Stonybrook, N.Y.), followed by extensive dialysis to remove unreacted peptide. Immunoreactivity was detected on 1-µm epoxy sections of marmoset spinal cord tissue and active MS lesions. For this, sections were etched with sodium ethoxide, equilibrated in $PO_4$-buffered saline containing 0.05% Triton X-100, and blocked with 10% normal rabbit serum. Sections were incubated with peptide-immunogold conjugates (1:100 in buffer) for 2 hours at room temperature. After washing, detection was performed by using silver enhancement (Nanoprobes). Sections were counterstained with toluidine blue. For the detection of IgG, sections were reacted with gold-labeled anti-monkey or anti-human IgG (Nanoprobes) at 1:100.

As controls, sections were either pretreated with unlabeled encephalitogenic MOG peptides or MBP to block the reaction, reacted with unlabeled nonencephalitogenic MOG peptide (aa 101–120) before application of the gold conjugates, or treated with gold-labeled irrelevant antigens (histone or MSA) or irrelevant IgG (anti-goat). The specificity of the labeling with the gold conjugates of encephalitogenic MOG peptides was also assessed in western blots where the MOG protein was first reacted with immune marmoset serum. Full details of the test and control reagents used to determine the specificity of the immunoreactivity can be found in Genain et al., Nature Med. 5:170–175 (1999).

Sections from the lumbar region of the spinal cord from the animals were obtained. The positive reactivity (brown coloration) of vesiculated myelin around axons (arrows), indicated the presence of IgG. Non-demyelinating axons did not stain. Positive reactivity for IgG was specifically found over the vesiculated networks of disrupted myelin surrounding axons.

We next identified the target antigens bound by these immunoglobulins by the application of immunogold-labeled conjugates of selected peptides of MOG and myelin basic protein (MBP). These myelin antigens were directly labeled with the gold particles on their primary $NH_2$ residues and were used to detect antigen-specific autoantibody in situ. With this technique, three separate gold-conjugated peptides of MOG were co-localized over the networks of disintegrating myelin sheaths in a pattern similar to that observed for gold-conjugated anti-IgG.

These peptides contained the amino acid sequences of MOG recognized by demyelinating antibodies that develop in serum of MOG-immunized marmosets (aa 1–20, aa 21–40 and aa 61–80). The gold-conjugated MOG peptide (aa 21–40) used has a sequence conserved across species. MOG-reactive droplets were also seen in surrounding macrophages, indicating the presence of internalized myelin debris to which anti-MOG antibody was bound. Positive reactivity with the labeled antigen indicated the presence of MOG-specific antibody in situ on vesicular myelin around axons and on myelin debris within the extracellular space and macrophages. Normal myelin (around the majority of the fibers) was not stained.

In contrast, gold-labeled conjugates of a peptide containing an immunodominant epitope of human MBP (aa 82–101, conserved across primate species) and of a control peptide of mouse serum albumin (MSA, aa 560–574), failed to label myelin membranes or macrophages. Thus, the vesiculated myelin networks are unstained (arrows) by either the gold-conjugated peptide of MBP or the gold-conjugated peptide of MSA.

These observations demonstrate in this non-human primate model of EAE that antibodies specific to MOG are in direct contact with the disintegrating myelin membranes and indicate that formation of the vesiculated membranous networks resulted from lytic attack by these autoantibodies.

MOG-specific autoantibodies are associated with myelin vesiculation in lesions of acute human MS. We next investigated with similar immunogold labeling the presence of MOG- and MBP-specific autoantibodies in CNS tissue obtained at biopsy or autopsy from patients with MS. As in marmoset EAE, gold-conjugated anti-IgG labeled the membranous myelin networks around single demyelinating axons, along with droplets of myelin debris scattered throughout the parenchyma. IgG is localized along the disintegrated myelin sheath of an axon cut in longitudinal section; cytoplasm of an hypertrophied astrocyte; tangential section of an oligodendrocyte. Densely stained IgG-coated myelin debris are visible in the parenchyma and in 3 macrophages (probably ameboid microglia). In addition, occasional plasma cells showed positive staining by anti-IgG. With the immunogold-labeled myelin antigen conjugates, vesiculated myelin networks were intensely stained by gold-conjugated-MOG peptides, and to a lesser extent by gold-conjugated MBP but not by MSA.

IgG-myelin complexes labeled with gold-conjugates of MOG and MBP were also present in macrophages but not in astrocytes or oligodendrocytes. No MOG- or MBP-labeled plasma cells were encountered. Reactivity with gold-conjugates was not observed in normal appearing MS white matter or around perivascular inflammatory cuffs. In marmosets immunized against whole myelin, a similar pattern of both anti-MOG and anti-MBP Ig deposition was observed. CNS tissue from amyotrophic lateral sclerosis, another neurologic disorder associated with white matter damage and macrophage activity, failed to show myelin antigen- specific immunogold reactivity. These findings directly identify MOG-specific antibodies in actively demyelinating lesions of human MS, indicating that, as in MOG-induced EAE, these autoantibodies play a causal role in the formation of small vesicles in the disrupted myelin sheaths. Soluble and B-cell surface Ig with anti-MBP specificity have been described in MS brain tissue, and in the current study, MBP-specific Ig was localized within the vesiculated myelin networks in MS lesions. Although anti-MBP antibodies have not been shown experimentally to initiate demyelinating pathology, these autoantibodies can mediate separate pathogenic mechanisms such as receptor-mediated phagocytosis by macrophages and/or presentation of myelin autoantigens to specific T-cells.

It is noteworthy that autoantibodies appear to be bound exclusively to the small vesicles that characterize the stage of complete disintegration of the myelin membranes, and to the myelin debris present either in the extracellular space or in phagocytic cells. Interestingly, similar but less extensive vesiculation of myelin was reported in earlier studies of rodent EAE where it was perceived as a transient early phenomenon. However, in the marmoset where lesion formation is protracted and ever expanding, the disrupted myelin was found consistently. The large scale vacuolation of myelin at the lesion margin among normally myelinated fibers occurred in the absence of significant local cellular infiltration or IgG deposition, and has also been reported at the edge of active MS lesions. This change in the myelin structure could be mediated by soluble factors diffusing from the center of the demyelinating plaque or from activated glial cells at the edge of the lesion. Morphologic changes similar to these large vacuoles have been reported in myelinated CNS cultures exposed to TNF-alpha and to a lesser degree, in cultures exposed to serum from animals with EAE and from subjects with MS.

Many of the therapeutic approaches targeting pathogenic T-cell responses in EAE models have not yet translated into successful treatment for human MS, perhaps suggesting that other components of the immune system need to be taken into account. B-cell responses appear to be a key factor for severity of clinical disease and pathology in *C. jacchus* EAE. The current results underscores the role of autoantibodies in the widespread destruction of myelin in MS, and emphasizes that in diseases that are initiated by T-cell responses, antibodies against critical antigens of the target organ are essential for development of irreversible tissue damage.

In vivo Administration of MOG-specific F(ab')$_2$ Fragments. Marmosets were administered 1 mg MBP in CFA containing *B. Pertussis* at Day 0 inducing non-demyelinating EAE. On Day 21 the animals were administered intravenously 0.17 mmol/kg of the F(ab')$_2$ from either 8.18.C5, a murine monoclonal anti-MOG antibody, or an anti-Influenza-A (control) antibody, then administered 0.17 mmol/kg 8.18.C5 antibody followed by a second intravenous administration of the appropriate F(ab')$_2$ for two hours. The animals were euthanized on day 35. Tissue samples were prepared as described in Example 3. Using high resolution microscopy and immunogold-labeled peptides of myelin antigens capable of detecting antigen-specific antibodies in situ, we have identified autoantibodies specific for myelinioligodendrocyte glycoprotein (MOG) around individual demyelinating axons in acute lesions of both human MS and marmoset EAE, where they appear directly responsible for the disintegration of myelin sheaths. Animals treated with control F(ab')$_2$ fragments, i.e., directed against influenza antigen, revealed large demyelinating plaques in the cervical spinal cord, and animals treated with MOG-specific F(ab')$_2$ fragments showed that the demyelinating activity of anti-MOG antibody in marmosets is dependent on intact Fc fragment function, as it can be competitively blocked in vivo by administration of MOG-specific F(ab')$_2$ fragments. These findings underscore the role of myelin-specific autoantibodies in the widespread destruction of myelin in MS and provide a basis for protective therapy in CNS demyelinating disorders.

Encephalitogenic Epitope Determination (MOG) in MS-like marmoset EAE. In *C. jacchus* marmosets with demyelinating EAE induced with recombinant rat MOG (rMOG: extracellular domain aa 1–125), the fine specificities of T-cell reactivity (proliferative responses in PBMC) and B-cell reactivity (serum antibody) to MOG were serially studied using overlapping 15-mer PIN-peptides (offsets of 1 and 3), corresponding to arnino-acid sequences of both rat and human MOG (Chiron Mimotopes, San Diego, Calif.). Results: All animals studied (n=6) had a prominent and sustained T-cell response restricted to aa 27–36, a sequence totally conserved across species. A single marmoset responded to a second T-cell epitope located within aa 62–72. Serum antibody responses (n=10) mapped to 4 different regions of MOG including 2 major epitopes, aa 13–21 and aa 62–74 (100% and 60% of animals, respectively) and additional epitopes were identified in some animals (aa 28–36 and 40–45). No epitope spreading was observed either for T-cells or antibodies in animals with relapsing EAE that were monitored for up to 93 days. Conclusions: Encephalitogenic responses to MOG in MS-like, marmoset EAE appear restricted to a limited number of B-cell and T-cell epitopes. These findings demonstrate feasibility of specific immunotherapy in human MS.

Detecting B-cells with surface bound antibodies. Early in the immune response B-cells have on their surface immunoglobulins that may specifically react with antigens. The B-cell immunoglobulin reacting with a self-antigen may be the first step in an autoimmune disease. Thus, early detection of autoantibodies on the surface of B-lymphocytes may provide the means to design a method of treatment before the onset of symptoms.

B-cells constitute about 3–5% of lymphocytes and were positively selected from freshly isolated peripheral blood mononuclear cells (PBMC) obtained from *C. jacchus* marmosets with MOG-induced EAE, from humans with MS and from healthy controls using anti-CD 19 coated beads. Antibodies to any other suitable B-cell marker may be used. Slides containing $2 \times 10^5$ B-cells (>98% purity) were fixed with 1% glutaraldehyde and washed. Alternatively, unfixed cells may be used. The isolated B-cells were then incubated with labeled immunogold conjugates of a mixture of eleven 20-mer overlapping peptides corresponding to the sequence of the $NH_2$ terminus of human MOG (1–120); identical B-cell preparations were labeled with control polypeptides corresponding to the sequence of histone or MBP peptides. Slides were enhanced with silver and labeled B-cells were counted by two different blind observers.

B-cells expressing MOG-specific surface immunoglobulins were easily detected with the gold-conjugated MOG peptides in PBMC from MOG-immunized marmosets (n=8). In these animals which are known to develop serum anti-MOG antibodies, circulating MOG-specific B-cells occurred at a frequency of about 1:500 to about 1:2,000, increased from 0–1:10,000 in healthy, unimmunized marmosets (n=8). Unlabeled MOG peptides added in excess completely inhibited labeling and gold-conjugated control protein failed to label any B-cell. In humans, circulating MOG-specific B-cells could be detected in 8 of 17 MS patients (47%) and 9 of 18 healthy controls (50%). The frequency of these autoreactive B-cells ranged from about 1:11,000 to about 1:200,000 B-cells, with the highest frequencies observed in two patients with relapsing-remitting MS (1:16,000 and 1:11,000, respectively).

This immunogold assay sensitively detects MOG-specific B-cells in peripheral blood. This assay has a sensitivity of about 1:500, preferably of about 1:2,000, more preferably about 1:10,000, even more preferably about 1:15,000, and most preferably about 1:200,000. In humans, autoreactive B-cells can be detected in approximately 50% of individuals, and are equally present in MS patients and controls. This suggests that the presence of anti-MOG antibodies in the nervous system of individuals with MS is not associated with a major expansion of MOG-reactive B-cells in the peripheral blood. The high frequency of MOG-reactive B-cells observed in PBMC provides new support for the hypothesis that MOG is an important autoantigen in humans.

In the Examples above, MOG-specific antibodies were exclusively localized to areas where the transformation of compact myelin into small vesicles around single demyelinating axons occurred, and to myelin debris either floating in the CNS parenchyma or internalized by phagocytic cells (macrophages and microglia). Thus, in addition to a direct lytic attack on myelin and oligodendrocytes, these antibodies can also be responsible for receptor-mediated phagocytosis by macrophages, or antibody-dependent cellular cytotoxicity, which have long been recognized as possible effector mechanisms of myelin damage. Our experiments using passive transfer of antibody in the *C. jacchus* system have shown that it is possible to competitively block pathogenic effects of the monoclonal anti-MOG antibody 8.18.C5 by in vivo administration of purified 8.18.C5-F(ab')$_2$ fragments, indicating that intact Fc fragments and not the MOG-specific CDR3 sequence themselves mediate the damage to myelin. Based on these findings, analogs or competitive inhibitors of antibody binding that are devoid of toxic effects on myelin provide a rational approach for therapy in EAE and related demyelinating disorders. Thus, the present invention utilizes compositions of autoantigen epitopes, anti-autoantigen antibody fragments or combinations thereof to effectuate treatment of demyelinating autoimmune diseases.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Accordingly, it is intended that the scope of the present invention be limited solely by the scope of the following claims, including equivalents thereof.

What is claimed is:

1. A method of inhibiting demyelination associated with the binding of an autoantibody to a myelin oligodendrocyte glycoprotein (MOG) polypeptide, comprising the step of administering to a marmoset or human host, subject to a pathogenic MOG polypeptide—polyclonal autoantibody binding, an effective amount of a composition comprising a MOG polypeptide-specific antibody fragment not having a functional Fc portion and sufficient to specifically bind the MOG polypeptide and competitively inhibit the binding of the autoantibody to the MOG polypeptide, whereby the demyelination is inhibited.

2. A method according to claim 1, wherein the fragment is selected from the group consisting of Fv, F(ab')$_2$, F(ab), F(ab)$_2$ and a fragment thereof sufficient to specifically bind the MOG polypeptide and competitively inhibit the binding of the autoantibody to the MOG polypeptide.

* * * * *

UNITED STATES PATENT AND TRADEMARK OFFICE
CERTIFICATE OF CORRECTION

PATENT NO.    : 6,333,033 B1
DATED         : December 25, 2001
INVENTOR(S)   : Claude P. Genain et al.

It is certified that error appears in the above-identified patent and that said Letters Patent is hereby corrected as shown below:

<u>Column 1,</u>
Line 2, insert the following statement:
-- This invention was made with Government support under Grant No. AI 43073, awarded by the National Institutes of Health. The Government has certain rights in this invention. --

Signed and Sealed this

Twentieth Day of August, 2002

*Attest:*

*Attesting Officer*

JAMES E. ROGAN
*Director of the United States Patent and Trademark Office*